US012797522B2

(12) United States Patent
Usman et al.

(10) Patent No.: US 12,797,522 B2
(45) Date of Patent: Nov. 17, 2026

(54) IDENTIFICATION SYSTEMS, INCLUDING ANTI-COUNTERFEIT AND ANTI-REUSE IDENTIFICATION SYSTEMS FOR AUTOMATED PERITONEAL DIALYSIS SYSTEMS, AND ASSOCIATED SYSTEMS, DEVICES, AND METHODS

(71) Applicant: Byonyks Medical Devices, Inc., Itasca, IL (US)

(72) Inventors: Farrukh Usman, Chatham, NY (US); Faisal Bashir, Lahore (PK); Abdul Qadeer, Lahore (PK); Salar Toor, Lahore (PK)

(73) Assignee: Byonyks Medical Devices, Inc., Itasca, IL (US)

( * ) Notice: Subject to any disclaimer, the term of this patent is extended or adjusted under 35 U.S.C. 154(b) by 713 days.

(21) Appl. No.: 18/041,024

(22) PCT Filed: Aug. 18, 2021

(86) PCT No.: PCT/US2021/046521
§ 371 (c)(1),
(2) Date: Feb. 8, 2023

(87) PCT Pub. No.: WO2022/040325
PCT Pub. Date: Feb. 24, 2022

(65) Prior Publication Data

US 2023/0302206 A1 Sep. 28, 2023

Related U.S. Application Data

(60) Provisional application No. 63/067,341, filed on Aug. 19, 2020.

(51) Int. Cl.
*A61M 1/14* (2006.01)
*G16H 40/40* (2018.01)

(52) U.S. Cl.
CPC ............ *A61M 1/152* (2022.05); *G16H 40/40* (2018.01)

(58) Field of Classification Search
CPC ........ A61M 1/152; G16H 40/40; G16H 20/17; G16H 20/40; G16H 40/20; G16H 40/63; G16H 40/67
(Continued)

(56) References Cited

U.S. PATENT DOCUMENTS 4,850,972 A 7/1989 Schulman et al.
6,468,241 B1 * 10/2002 Gelfand ................ A61M 1/154 604/6.11
(Continued)

FOREIGN PATENT DOCUMENTS

WO 2021211803 A1 10/2021
WO 2022027036 A1 2/2022
(Continued)

OTHER PUBLICATIONS

Written Opinion and International Search Report dated Mar. 24, 2022 for International Patent Application No. PCT/US2021/046521.

*Primary Examiner* — Eric Blount

(57) ABSTRACT

Identification systems, including anti-counterfeit and anti-reuse identification systems for automated peritoneal dialysis (APD) systems, and associated systems, devices, and methods are disclosed herein. In one embodiment, an APD system includes an identification system having at least one identification sensor configured to read device identifiers associated with disposable components of the APD system. The disposable components can include cassettes or source bags containing dialysate solution. In some embodiments, the identification system can (a) compare a device identifier of a disposable component to a whitelist of valid device identifiers, (b) determine whether the device identifier is
(Continued)

valid, unused, and/or non-expired, and/or (c) based on the determination, determine whether to use the disposable component to execute an exchange treatment. In some embodiments, the APD system can include (i) a mount configured to receive the disposable component and (ii) a plunger mechanism configured to physically damage the disposable component after it has been used.

21 Claims, 10 Drawing Sheets

(58) Field of Classification Search
USPC ................. 604/29, 19, 27, 503; 340/539.12; 210/321.71, 647, 85
See application file for complete search history.

(56) References Cited

U.S. PATENT DOCUMENTS

| | | | | |
|---|---|---|---|---|
| 7,762,989 | B2 * | 7/2010 | Simpson | A61M 39/287 604/151 |
| 7,935,074 | B2 * | 5/2011 | Plahey | A61M 1/28 604/29 |
| 8,330,579 | B2 * | 12/2012 | Kneip | A61M 1/152 604/29 |
| 8,882,700 | B2 * | 11/2014 | Chapman | A61M 1/155 604/27 |
| 10,089,443 | B2 | 10/2018 | Miller et al. | |
| 11,690,941 | B2 * | 7/2023 | Burbank | A61M 1/281 604/29 |
| 2001/0020148 | A1 | 9/2001 | Sasse et al. | |
| 2001/0040127 | A1 * | 11/2001 | Donig | A61M 1/1668 210/321.71 |
| 2002/0038392 | A1 * | 3/2002 | De La Huerga | G16H 20/17 710/8 |
| 2003/0088203 | A1 * | 5/2003 | Gelfand | A61M 1/3621 604/6.09 |
| 2005/0277873 | A1 * | 12/2005 | Stewart | A61M 5/142 604/93.01 |
| 2006/0224128 | A1 * | 10/2006 | Lurvey | A61M 39/287 604/250 |
| 2008/0061153 | A1 | 3/2008 | Hickle et al. | |
| 2009/0043253 | A1 * | 2/2009 | Podaima | G16H 10/60 604/67 |
| 2009/0204075 | A1 * | 8/2009 | Simpson | A61M 5/162 604/151 |
| 2009/0275883 | A1 * | 11/2009 | Chapman | A61M 1/155 340/539.12 |
| 2015/0359954 | A1 * | 12/2015 | Gerber | A61M 1/36 210/85 |
| 2016/0210106 | A1 | 7/2016 | Hampapuram et al. | |
| 2019/0295256 | A1 * | 9/2019 | Yang | G06K 7/1413 |

FOREIGN PATENT DOCUMENTS

| | | | |
|---|---|---|---|
| WO | 2022040325 | A2 | 2/2022 |
| WO | 2022040597 | A1 | 2/2022 |
| WO | 2022040601 | A1 | 2/2022 |
| WO | 2022051456 | A1 | 3/2022 |

* cited by examiner

IDENTIFICATION SYSTEMS, INCLUDING ANTI-COUNTERFEIT AND ANTI-REUSE IDENTIFICATION SYSTEMS FOR AUTOMATED PERITONEAL DIALYSIS SYSTEMS, AND ASSOCIATED SYSTEMS, DEVICES, AND METHODS

CROSS-REFERENCE TO RELATED APPLICATION(S)

This application is a 371 U.S. national phase of PCT/US2021/046521, filed Aug. 18, 2021, which claims the benefit of priority from U.S. Provisional application No. 63/067,341, filed Aug. 19, 2020, both which are incorporated by reference in its their entirety.

TECHNICAL FIELD

The present disclosure is directed to identification systems, and associated systems, devices, and methods. For example, several embodiments of the present technology are directed to identifications systems for identifying and preventing use of counterfeit, previously used, and/or expired disposables (e.g., source bags, cassettes, damping devices, etc.) in automated peritoneal dialysis (APD) systems.

BACKGROUND

Dialysis is used to (a) remove excess fluid and toxins in persons with kidney failure and (b) correct electrolyte concentrations in their blood. Peritoneal dialysis is a form of dialysis that uses a peritoneum in an individual's abdomen as a membrane through which fluid and dissolved substances are exchanged with blood. More specifically, a solution is introduced into and removed from the individual's abdomen via a surgically-installed catheter.

In continuous ambulatory dialysis (CAPD), solution is manually introduced and removed (e.g., at regular intervals throughout the day). In particular, the catheter is connected to a disposable set that includes (i) a source bag (e.g., hung on a drip stand) containing new solution, (ii) a drain bag configured to collect waste solution, and (iii) various fluid lines connecting the source bag and the drain bag to the catheter. Waste solution from the individual's lower abdomen is drained into the drain bag via the catheter, and new solution is introduced into the individual's lower abdomen via the catheter. After such an exchange treatment is complete, the disposable set is discarded.

APD (also known as continuous cycling peritoneal dialysis (CCPD)) is similar to CAPD except that the exchange treatment is automated using an APD machine or cycler. More specifically, a pump included in the APD machine is used to introduce and remove the solution (e.g., while the individual sleeps). Each APD exchange treatment may include one or more cycles of introducing and removing solution from the individual's abdomen.

BRIEF DESCRIPTION OF THE DRAWINGS

Many aspects of the present disclosure can be better understood with reference to the following drawings. The components in the drawings are not necessarily to scale. Instead, emphasis is placed on clearly illustrating the principles of the present disclosure. The drawings should not be taken to limit the disclosure to the specific embodiments depicted, but are for explanation and understanding only.

DETAILED DESCRIPTION

Figure 1A:
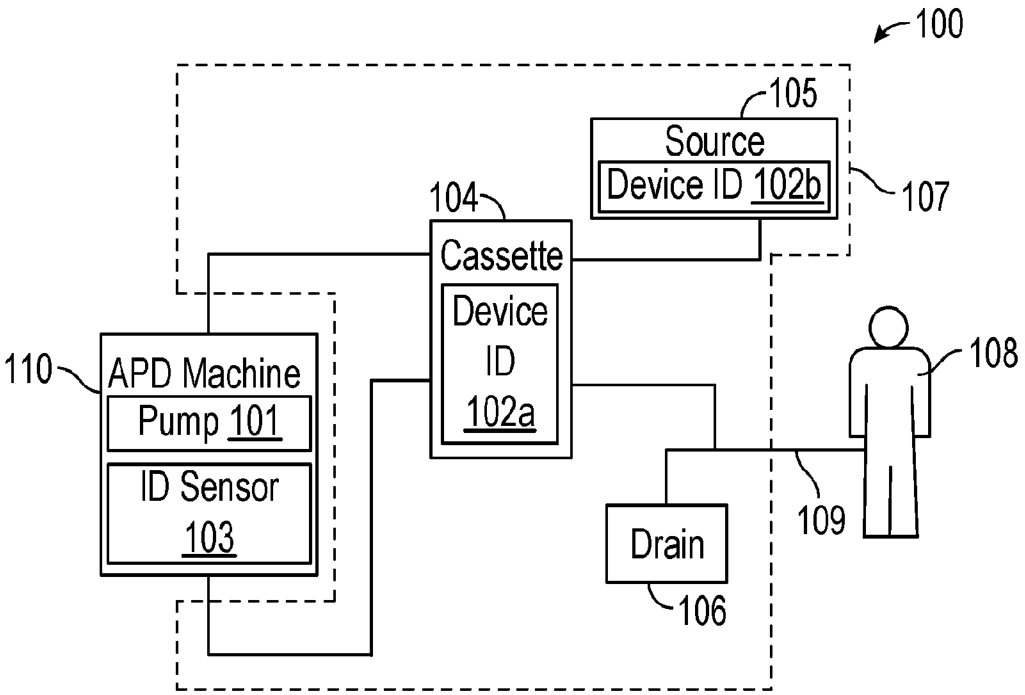
FIG. 1A is a partially schematic representation of an APD system configured in accordance with various embodiments of the present technology.

The present disclosure is directed to identification systems, and associated systems, devices, and methods. In the illustrated embodiments below, identification systems of the present technology are primarily described in the context of identifying and preventing use of counterfeit, previously used, and/or expired disposables in APD systems. Identification systems configured in accordance with various embodiments of the present technology, however, can be incorporated into and/or used by other systems, including CAPD systems, hemodialysis systems, and/or other medical or non-medical systems. Furthermore, a person skilled in the art will understand (i) that the technology may have additional embodiments than illustrated in FIGS. 1A-9 and (ii) that the technology may be practiced without several of the details of the embodiments described below with reference to FIGS. 1A-9.

A. Overview

Many medical systems include single-use, disposable sets or components. For example, APD systems include disposable sets that include source bags, drain bags, cassettes, damping devices, fluid lines, connectors, and/or other disposable components. These disposable sets are configured to introduce new solution (e.g., dialysate) into a patient and/or to remove waste solution from the patient. The disposable sets are then discarded after a single use to reduce the risk of introducing bacteria into the patient and/or to reduce the risk of components of the disposable sets malfunctioning during use.

Unfortunately, a market exists for counterfeited, reused, and/or expired disposable components for use in many medical systems, especially in locations lacking adequate regulation and governance of medical devices. To reduce costs, counterfeited goods are often manufactured with inferior quality. As such, the risk that these counterited goods malfunction during use is heightened in comparison to the legitimate products of higher quality. This can lead to defamation of the manufacturer or vendor producing or selling legitimate versions of the product, and/or to damage of consumer loyalty to an established brand. Similarly, reused and expired products pose a risk to patient health for obvious reasons.

To address these concerns, the inventors of the present technology have developed identification systems, including anti-counterfeit and anti-reuse identification systems for APD systems. In one embodiment, for example, an identification system of an APD system includes an identification sensor configured to read a device identifier of a disposable component, such as a cassette or source bag. The identification sensor can be included in an APD machine of the APD system and/or on a computing device (e.g., a mobile phone) of an operator of the APD system. The device identifier can be unique to the disposable component and/or readable by only a manufacturer of the disposable component, an authorized user (e.g., a licensee), or an identification sensor or system specifically configured to decode information included in the device identifier. After reading the device identifier, the identification system can cross-reference the device identifier against a whitelist of valid device identifiers stored locally (e.g., on the APD machine, on the computing device, etc.) and/or remotely (e.g., on a server or database). If the whitelist indicates that the device identifier is valid, that the disposable component is unused, and/or that a solution or other product contained within the disposable component is not expired, the identification system can (a) permit use of the disposable component in an exchange treatment and (b) log use of the disposable component in the whitelist such that the disposable component cannot be reused in the future. On the other hand, if the whitelist indicates that the device identifier is invalid, that the disposable component has been previously used, and/or that the solution or other product within the disposable component is expired, the identification system can reject the disposable component and prevent use of the disposable component in an exchange treatment.

In some embodiments, the identification system can include a mount configured to receive a disposable component, such as a cassette. The mount can include an installation sensor to determine whether the disposable component is properly installed within the mount. The mount can include a plunger mechanism having a puncture feature. After the disposable component is used in an exchange treatment and before the disposable component is released from the mount, the plunger mechanism can be actuated to physically damage the disposable set such that it cannot be used to execute a future exchange treatment.

Therefore, embodiments of the present technology are expected to prevent use of counterfeited, used, and/or expired disposable components in therapy sessions executed by an APD system. Additionally, or alternatively, embodiments of the present technology log use of disposable components and/or physically damage disposable components after they have been used such that the disposable components cannot be reused in future therapy sessions. As a result, it is expected that the present technology will reduce, minimize, and/or eliminate risks to patient health presented by use of counterfeited, used, and/or expired disposable components during exchange treatments executed by an APD system. In turn, the present technology is further expected to protect a company's reputation and/or consumer brand loyalty against damage posed by counterfeit, used, and/or expired disposable components.

B. Selected Embodiments of Pressure Sensors, Including Pressure Sensors for APD Systems, and Associated Systems, Devices and Methods FIG. 1A is a partially schematic representation of an APD system 100 ("the system 100") configured in accordance with various embodiments of the present technology. As shown, the system 100 includes an APD machine or cycler 110 and a disposable set 107. The disposable set 107 of FIG. 1A includes a cassette 104, a source bag 105, a drain bag 106, and various fluid lines extending between components of the disposable set 107 and/or the APD machine 110. Other well-known components of APD systems are not illustrated in FIG. 1A or described in detail below so as to avoid unnecessarily obscuring aspects of the present technology.

In some embodiments, the APD machine 110 can include a pump 101. The pump 101 can be a non-invasive pump. For example, the pump 101 can be a peristaltic pump or another suitable type of pump. In these and other embodiments, the pump 101 can be removably or permanently integrated into the APD machine 110. Alternatively, the pump 101 can be a component of the system 100 that is separate from the APD machine 110.

Various components of the disposable set 107 can interface with the APD machine 110. For example, as described in greater detail below, the cassette 104 can be installed in (e.g., held in place, attached to, supported by, etc.) a mount (not shown) of the APD machine 110 during an exchange treatment. The disposable set 107 can be configured to interface (a) with the pump 101 and (b) with a catheter 109 installed in a patient 108. For example, the disposable set 107 can (e.g., directly, or indirectly via a transfer set or catheter extension (not shown)) connect to the catheter 109 such that the catheter 109 is placed in fluid communication with the source bag 105 and/or the drain bag 106.

In operation, the system 100 can be configured to introduce solution (e.g., dialysate or another fluid initially contained within the source bag 105) into the patient 108 via the APD machine 110 (e.g., using the pump 101) and/or via at least a first portion of the disposable set 107. The system 100 can further be configured to remove solution from the patient 108 by draining the solution into the drain bag 106 using the APD machine 110 (e.g., using the pump 101) and/or via at least a second portion of the disposable set 107. In some embodiments, a single exchange treatment can include one or more cycles of introducing solution into the patient 108 and removing solution from the patient 108. After an exchange treatment is complete, the disposable set 107 can be discarded and a separate (e.g., a new) disposable set 107 can be used for a subsequent treatment.

As shown in FIG. 1A, the system 100 and/or the APD machine 110 can include one or more identification sensors 103 ("the ID sensor(s) 103"). In some embodiments, the ID sensor(s) 103 include optical sensors, such as image sensors, cameras, and/or scanners. In these and other embodiments, the ID sensor(s) 103 include other electronic sensors, such as radiofrequency (RF) receivers or transceivers and/or near-field communication (NFC) readers. As described in greater detail below, the ID sensor(s) 103 can be configured to read (e.g., sense, scan, measure, detect, etc.) one or more device or component identifiers 102 that can be used to decrease the likelihood that counterfeit, previously used, and/or expired components (e.g., disposables) are used in the system 100 to deliver and/or remove solution from the patient 108 during an exchange treatment. In the embodiment illustrated in FIG. 1A, the cassette 104 includes a device identifier (ID) 102*a,* and the source bag 105 includes a device ID 102*b*. The device ID 102*a* and/or 102*b* can be a radiofrequency identification (RFID) device, a quick response (QR) code, a barcode, a near-field communication (NFC) device, a digitally readable number, a marking, or another suitable identification device.

Figure 1B:
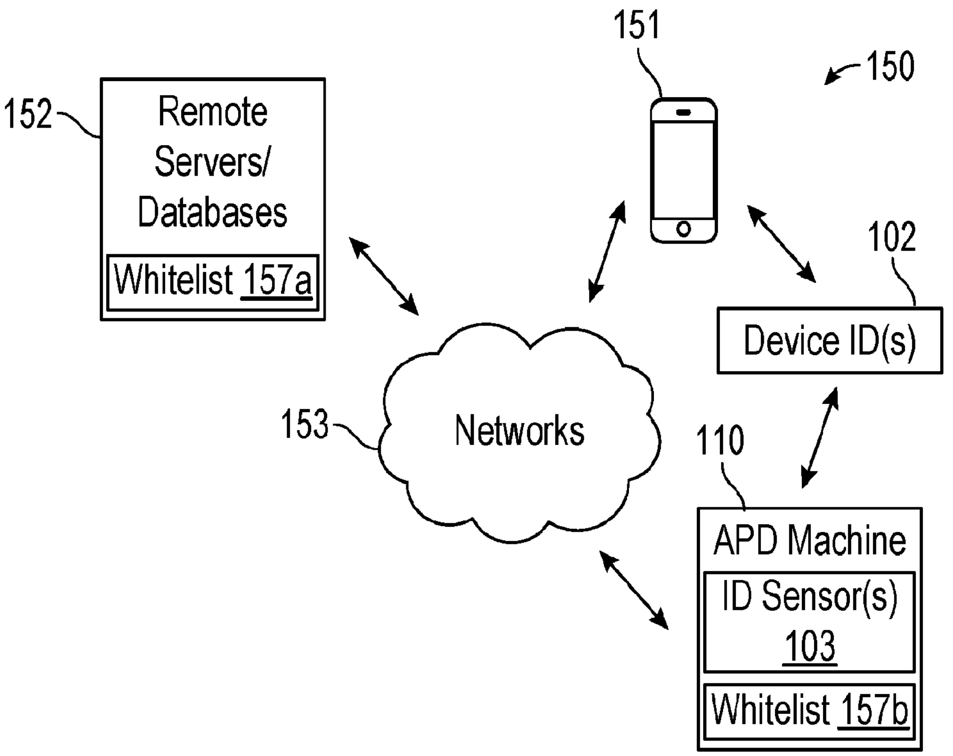
FIG. 1B is a partially schematic block diagram of a representative environment in Which the APD system of FIG. 1A operates.

FIG. 1B is a partially schematic block diagram of a representative environment 150 in which an identification system of the APD system 100 of FIG. 1A operates. In some embodiments, the identification system includes the APD machine 110, ID sensors 103, device IDs 102, one or more computing devices 151, one or more remote servers/databases 152, and/or one or more whitelists 157 of valid device IDs and/or other information. In the environment 150, the APD machine 110 of the system 100 can connect to (e.g., wirelessly and/or via one or more wires) and/or communicate with the one or more computing devices 151 over one or more networks 153, including public or private networks (e.g., the internet). The one or more computing devices 151 can include personal computers, server computers, handheld or laptop devices, cellular (e.g., mobile) telephones, wearable electronics, tablet devices, multiprocessor systems, microprocessor-based systems, set-top boxes, programmable consumer electronics, network PCs, minicomputers, mainframe computers, distributed computing environments that include any of the above systems or devices, or the like. In these and other embodiments, the one or more computing devices 151 can include other remote or local devices, such as landline phones, fax machines, medical devices, thermostats, speakers, and other devices.

As shown in FIG. 1B, the APD machine 110 of the system 100 can connect to and/or communicate with the one or more remote servers/databases 152 (e.g., directly and/or via one or more of the computing devices 151). In some embodiments, a remote server/database 152 can be an edge server which receives client requests and coordinates fulfillment of those requests through other servers. The remote servers/databases 152 can comprise computing systems. Although the remote servers/databases 152 are displayed logically as a single server/database, the remote servers/databases 152 can be a distributed computing environment encompassing multiple computing devices and/or databases located at the same or at geographically disparate physical locations. In some embodiments, the remote servers/databases 152 correspond to a group of servers.

In some embodiments, the one or more computing devices 151, the APD machine 110 of the system 100, and/or the remote servers/databases 152 can each act as a server or client to other server/client devices. The remote servers/databases 152 can include one or more databases. The one or more databases can warehouse (e.g. store) information such as user accounts/profiles; a whitelist 157*a* of valid device IDs 102, corresponding use identifiers or tags, and/or corresponding expiration dates; and/or other information. Additionally, or alternatively, the APD machine 110 (and/or the one or more computing devices 151) can store a local version (a "whitelist 157*b*") of the whitelist 157*a* stored in the remove servers/databases 152. For example, the whitelist 157*a* can be periodically (e.g., once a day, once a week, once a month, etc.) downloaded from the remote servers/databases 152 to the APD machine 110 (e.g., for use when the APD machine 110 is unable to connect to the remove servers/databases 152 over the networks 153). Additionally, or alternatively, the whitelist 157*b* can be periodically synced with the whitelist 157*a* such that any updates to the whitelist 157*a* can be reflected on the whitelist 157*b* (and vice versa) after the whitelists 157*a* and 157*b* are synced with one another.

The one or more networks 153 allow for communication in the environment 150. The one or more networks 153 can include one or more wireless networks, such as, but not limited to, one or more of a Local Area Network (LAN), Wireless Local Area Network (WLAN), a near-field communication (NFC) network, a body area network (BAN), a Personal Area Network (PAN), Campus Area Network (CAN), a Metropolitan Area Network (MAN), a Wide Area Network (WAN), a Wireless Wide Area Network (WWAN), Global System for Mobile Communications (GSM), Personal Communications Service (PCS), Digital Advanced Mobile Phone Service (D-Amps), Bluetooth. Wi-Fi, Fixed Wireless Data, 2G, 2.5G, 3G, 3.75G 4G, 5G, LTE networks, enhanced data rates for GSM evolution (EDGE), General packet radio service (GPRS), enhanced GPRS, messaging protocols such as, TCP/IP, SMS, MMS, extensible messaging and presence protocol (XMPP), real time messaging protocol (RTMP), instant messaging and presence protocol (IMPP), instant messaging, USSD, IRC, or any other wireless data networks or messaging protocols. Networks 153 may also include wired networks.

As shown in FIG. 1B, ID sensor(s) 103 included in the APD machine and/or in hardware or software of the one or more computing devices 151 can capture (e.g., read, communicate with corresponding circuits of, etc.) device IDs 102 corresponding to disposable components (e.g., the cassette 104 and/or the source bag 105 of the disposable set 107 of FIG. 1A) of the system 100. As described in greater detail below, the captured device IDs 102 can be communicated to the remote servers/databases 152 over the networks 153. In turn, the remote servers/databases 152 can cross-reference the captured device IDs 102 with the valid device IDs and/or other information stored in the whitelist 157*a* to determine (a) whether the corresponding disposable component is valid (e.g., legitimate) or a counterfeit, (b) whether the corresponding disposable component is new or has previously been used, and/or (c) whether the corresponding disposable component has or has not expired. The remote servers/databases 152 can communicate one or more of these determinations to the APD machine 110 and/or the one or more computing devices 151 via the networks 153. Alternatively, when the remote servers/databases 152 cannot be reached via the networks 153, the captured device IDs can be cross-referenced against information stored in the local whitelist 157*b*.

In turn, one or more of the above determinations can be used to determine whether to execute a therapy session using the corresponding disposable components. When a therapy session is executed, a use identifier or tag stored in the whitelist 157*a* and/or 157*b* and corresponding to the captured device ID 102 can be updated to reflect that the corresponding disposable component has been used. In this manner, the corresponding disposable component will be rejected by the system 100 if an operator attempts to reuse the disposable component for a future therapy session.

Figure 2:
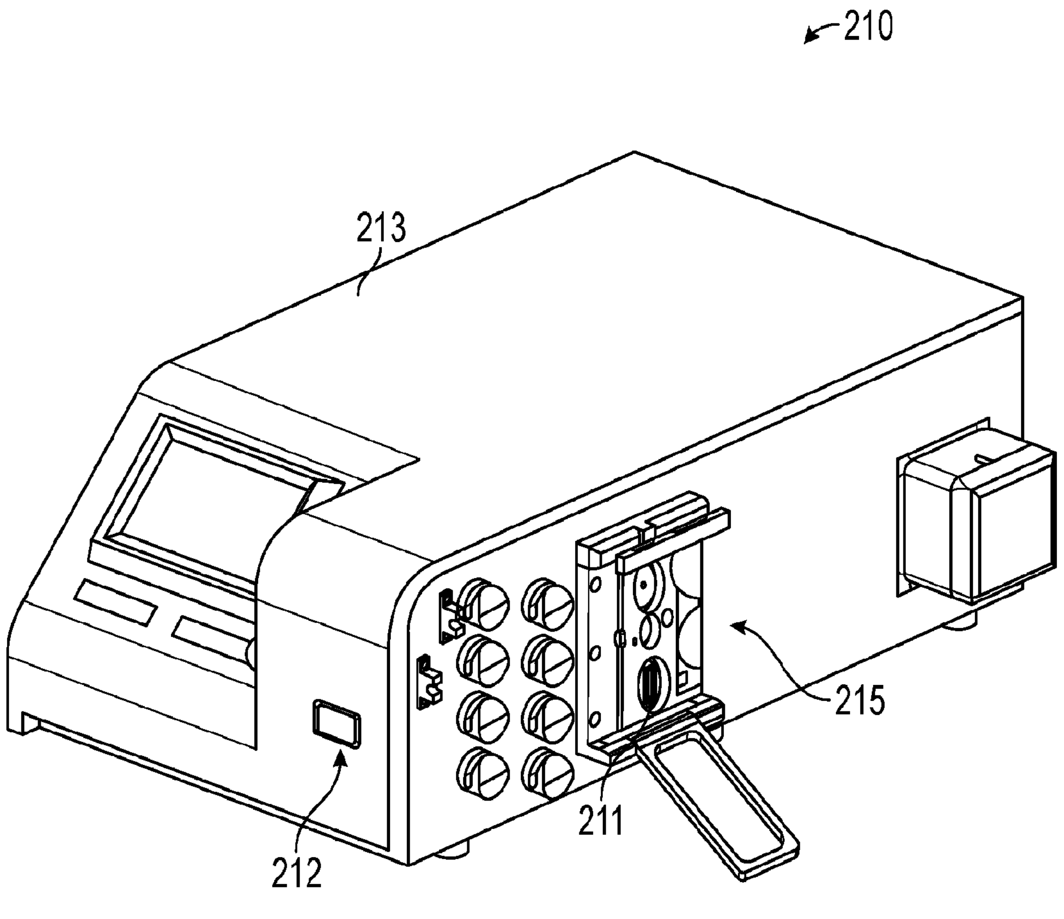
FIG. 2 is a partially schematic, perspective view of an APD machine configured in accordance with various embodiments of the present technology.

FIG. 2 is a partially schematic, perspective view of an APD machine 210 configured in accordance with various embodiments of the present technology. In some embodiments, the APD machine 210 can be the APD machine 110 of FIGS. 1A and 1B or another APD machine configured in accordance with the present technology. As shown in FIG. 2, the APD machine 210 includes a housing 213 and a mount 215 attached to, integrated with, or exposed through the housing 213. As discussed in greater detail below with respect to FIGS. 5A-6C, the mount 215 can be a locking mount and/or can be configured to releasably retain a cassette (e.g., the cassette 104 of FIG. 1A) and/or another disposable component (e.g., a damping device) of an APD system. The mount 215 is shown in an open configuration in FIG. 2 without a cassette or another component installed within the mount 215.

The APD machine 210 further includes ID sensors 211 and 212 attached to, integrated with, or exposed through the housing 213 and/or the mount 215. The ID sensor 211 and/or the ID sensor 212 can include an optical sensor, such as a scanner, an image sensor, or a camera. In these and other embodiments, the ID sensor 211 and/or the ID sensor 212 can include another type of sensor, such as an NFC reader or an RF receiver or transceiver. As discussed in greater detail below with respect to FIGS. 4A-5B, the ID sensor 211 is configured to read a device identifier that is (a) installed on a component (e.g., a cassette) of an APD system and (b) positioned (e.g., held, such as by the mount 215) proximate the ID sensor 211 and/or within a field of view of the ID sensor (e.g., while the component is installed in the mount 215). Similarly, as discussed in greater detail below with respect to FIGS. 7 and 8, the ID sensor 212 is configured to read a device identifier that is (a) installed on a component (e.g., a cassette, a source bag, a damping device, a drain bag, etc.) and (b) positioned (e.g., held, such as by an operator) proximate the ID sensor 212 and/or within a field of view of the ID sensor 212.

Although shown with both the ID sensor 211 and the ID sensor 212 in FIG. 2, the APD machine 210 in other embodiments of the present technology can include the ID sensor 211 in lieu of the ID sensor 212 (or vice versa). Additionally, or alternatively, the APD machine 210 can include one or more other ID sensors in addition to or in lieu of the ID sensor 211 and/or the ID sensor 212. Furthermore, the ID sensor 211 can be positioned at other locations within the mount 215 than shown in FIG. 2, and/or the ID sensor 212 can be positioned at other locations on the APD machine 210 than shown in FIG. 2. In these and other embodiments, the ID sensor 211 and/or the ID sensor 212 can be separate from the APD machine 210. For example, the ID sensor 211 and/or the ID sensor 212 can be included on (e.g., hardware of and/or a software application on) a separate computing device, such as a mobile phone, tablet, or computer of an operator of the APD machine 210 and/or an APD system.

Figure 3A:
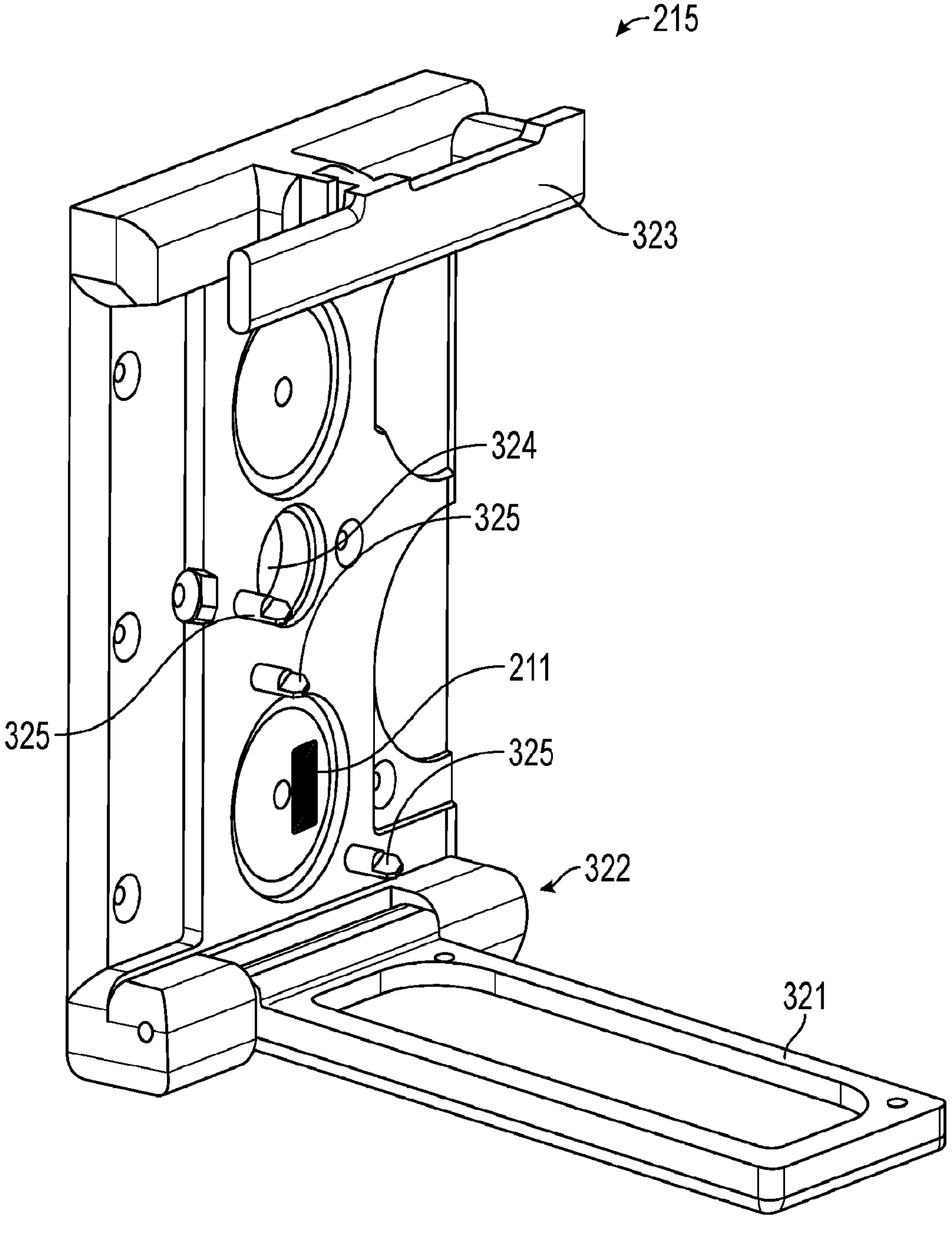
FIGS. 3A-3C are partially schematic, perspective views of a mount configured in accordance with various embodiments of the present technology.
Figure 3B:
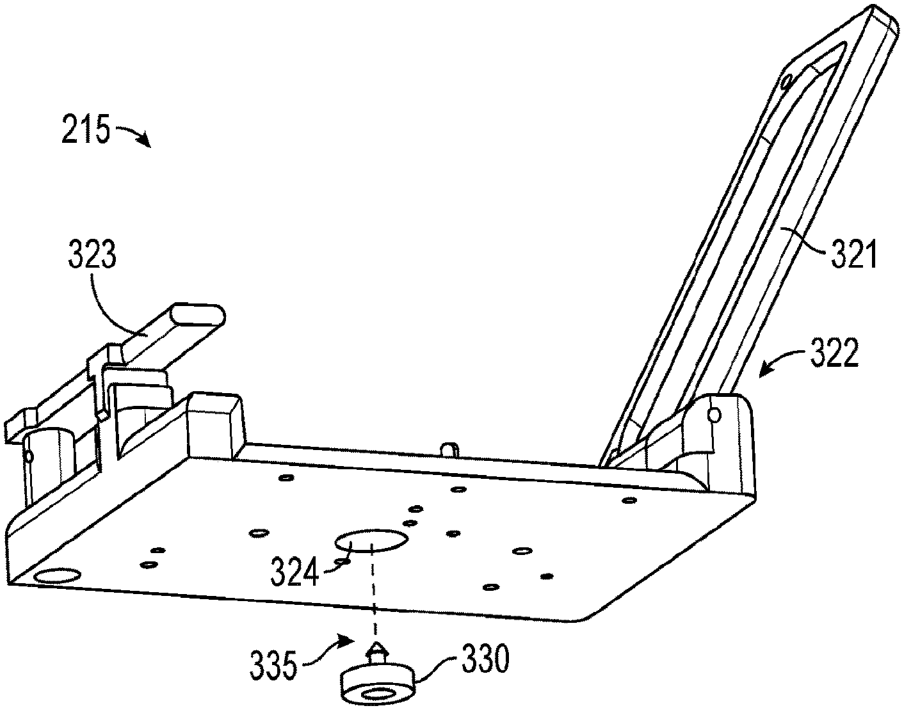
Figure 3C:
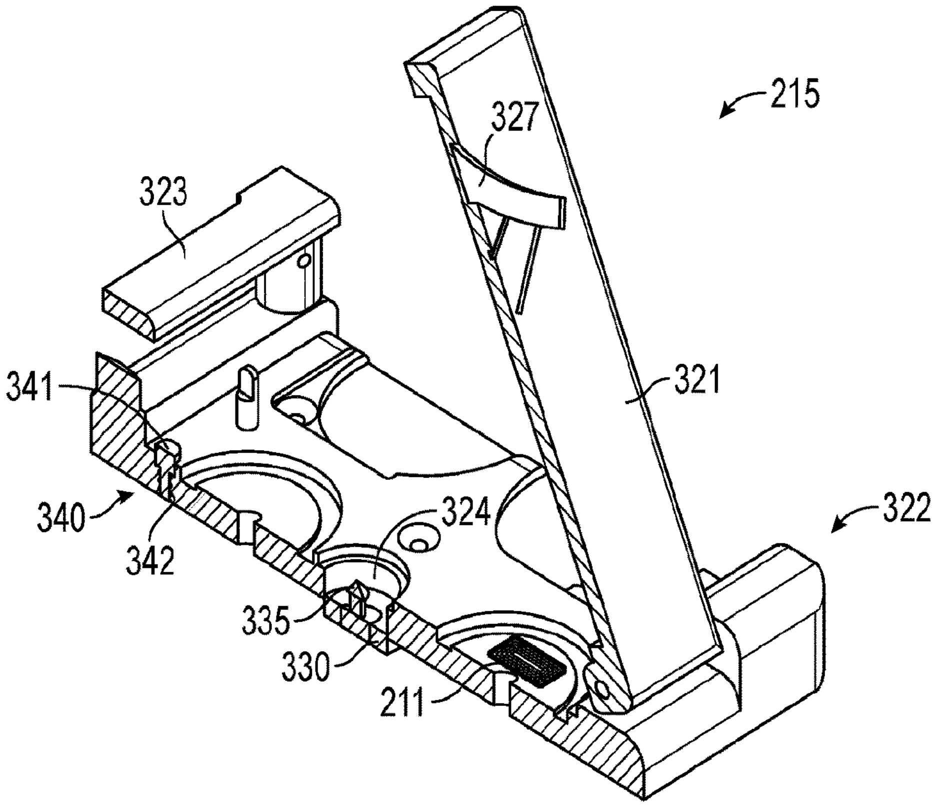
Figure 5A:
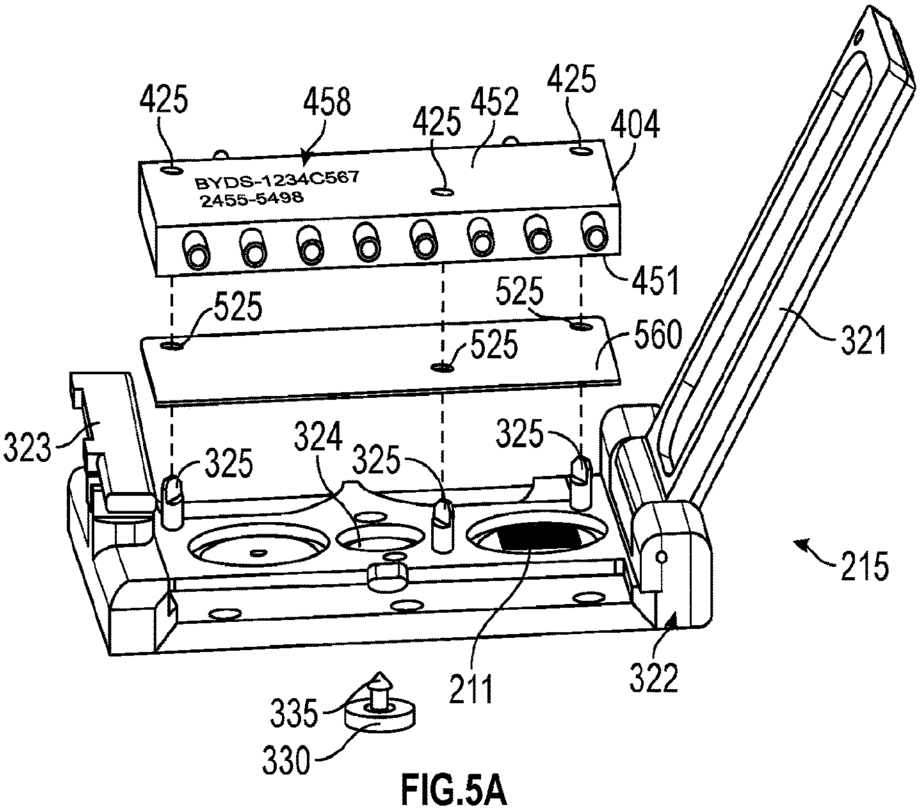
FIGS. 5A and 5B are partially schematic, perspective views of the cassette of FIGS. 4A and 4B being installed within the mount of FIGS. 3A-3C in accordance with various embodiments of the present technology.

FIGS. 3A-3C are partially schematic, perspective views of the mount 215 of FIG. 2 before installation with the housing 213. In some embodiments, the mount 215 includes an arm 321 that can transition (e.g., pivot) between an open position (FIGS. 3A-3C) and a closed position (e.g., as shown in FIG. 5A) about a hinge 322 or other translation mechanism. In some embodiments, the mount 215 includes a locking mechanism 323 that is configured to (a) rotate over the arm 321 when the arm 321 is in the closed position, (b) engage with a recess or slot 327 (FIG. 3C) on the arm 321, and/or (c) releasably retain the arm 321 in the closed position (e.g., to releasably retain a cassette or another component of an APD system within the mount 215).

As best shown in FIG. 3A, the mount 215 can include one or more alignment features 325. In the illustrated embodiment, the alignment features 325 are protrusions that are configured to engage or interface with corresponding recesses on a cassette or another component of an APD system. In other embodiments, the alignment features 325 can be recesses configured to engage or interface with corresponding protrusions on a cassette or another component of an APD system. In operation, the alignment features 325 can be used to facilitate (a) installation of a cassette or another component of an APD system within the mount 215 and/or (b) alignment of a device ID on the cassette or other component with the ID sensor 211.

Figure 4A:
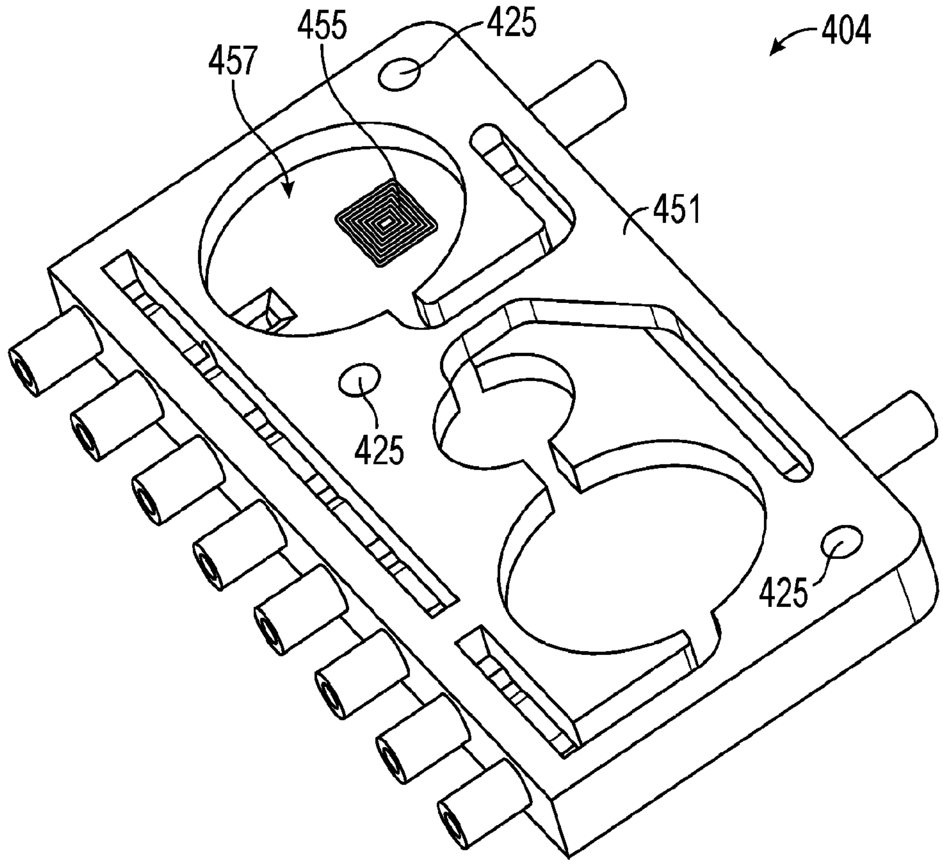
FIGS. 4A and 4B are partially schematic, perspective views of a cassette configured in accordance with various embodiments of the present technology.
Figure 4B:
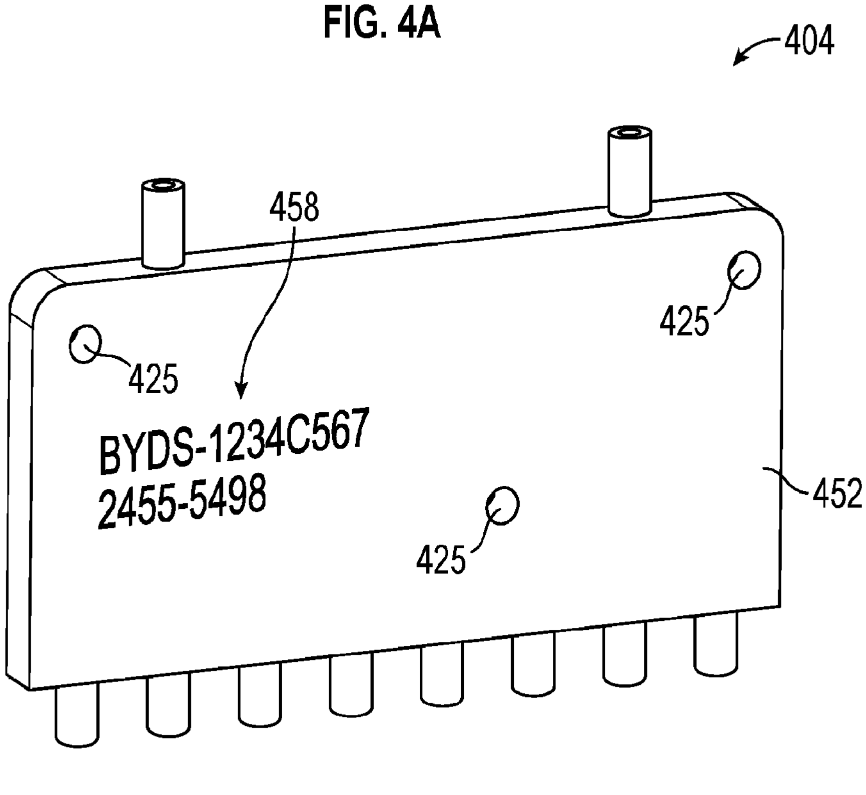

For example, FIGS. 4A and 4B are partially schematic, perspective views of a cassette 404 configured in accordance with various embodiments of the present technology. The cassette 404 can be the cassette 104 of FIG. 1A or another cassette of the present technology. In operation, the cassette 404 can be configured to control solution flow during an exchange treatment of an APD system (e.g., the system 100 of FIG. 1A).

Referring first to FIG. 4A, the cassette 404 includes a device identifier 455 ("the device ID 455") on a first side 451 of the cassette 404. The device ID 455 is positioned within a fluid cavity 457 of the cassette 404 in FIG. 4A, but the device ID 455 can be positioned at other locations along the cassette 404 in other embodiments. The device ID 455 can be a small battery-operated identification device attached to, integrated with, or exposed through the cassette 404. In these and other embodiments, the device ID 455 can be an RFID device, a QR code, an NFC device, a digitally readable number, or another suitable identification device. The device ID 455 can be programmed or otherwise manufactured with an identifier unique to the cassette 404. For example, the device ID 455 can be assigned a unique identifier that is randomly generated and/or is based at least in part on (a) a date and/or time of day the cassette 404 was manufactured and/or marked; (b) a batch number corresponding to the cassette 404; (c) information (e.g., name, employee ID, etc.) related to a worker assigned to the batch, and/or (d) other information. In some embodiments, the unique identifier can be encoded such that the device ID 455 can be read or interpreted by only a manufacturer of the device ID 455, another authorized party (e.g., a licensee), and/or an ID sensor (e.g., the ID sensor 211 and/or 212 of FIG. 2) or identification system specifically configured to read the device ID 455.

Referring now to FIG. 4B, the cassette 404 can include a device ID 458 ("the device ID 458") in addition to or in lieu of the device ID 455. The device ID 458 is positioned on a second side 452 of the cassette 404 opposite the first side 451, but the device ID 458 can be positioned at other locations along the cassette 404 in other embodiments. The device ID 458 can be a marking that is applied to (e.g., stamped onto, etched into, etc.) a surface of the cassette 404. More specifically, a marking machine (not shown) can mark the device ID 458 with a code unique to the cassette 404. The code can (a) be randomly generated and/or (b) include and/or be based at least in part on embedded information that can be unique to the cassette 404 and/or used to identify the cassette 404 (e.g., using the ID sensor 211 and/or the ID sensor 212 of FIG. 2). Information embedded into the code can include (a) a date and/or time of day the cassette 404 was manufactured and/or marked; (b) a batch number corresponding to the cassette 404; (c) information (e.g., name, employee ID, etc.) related to a worker assigned to the batch and/or (b) other changeable information. In some embodiments, the code and/or information embedded within the code can be encoded such that the code and/or the information can be read, decoded, and/or interpreted from the marking by only the manufacturer of the cassette 404, another authorized party (e.g., a licensee), and/or an ID sensor or identification system specifically configured to read the device ID 458.

As shown in FIGS. 4A and 4B, the cassette 404 can further include one or more alignment features 425. In the illustrated embodiment, the alignment features 425 are recesses that are configured to engage or interface with corresponding protrusion alignment features 325 (FIG. 3A) of the mount 215 (FIG. 3A). In other embodiments, the alignment features 425 of the cassette 404 can be protrusions configured to engage or interface with corresponding recess alignment features 325 of the mount 215.

Figure 5B:
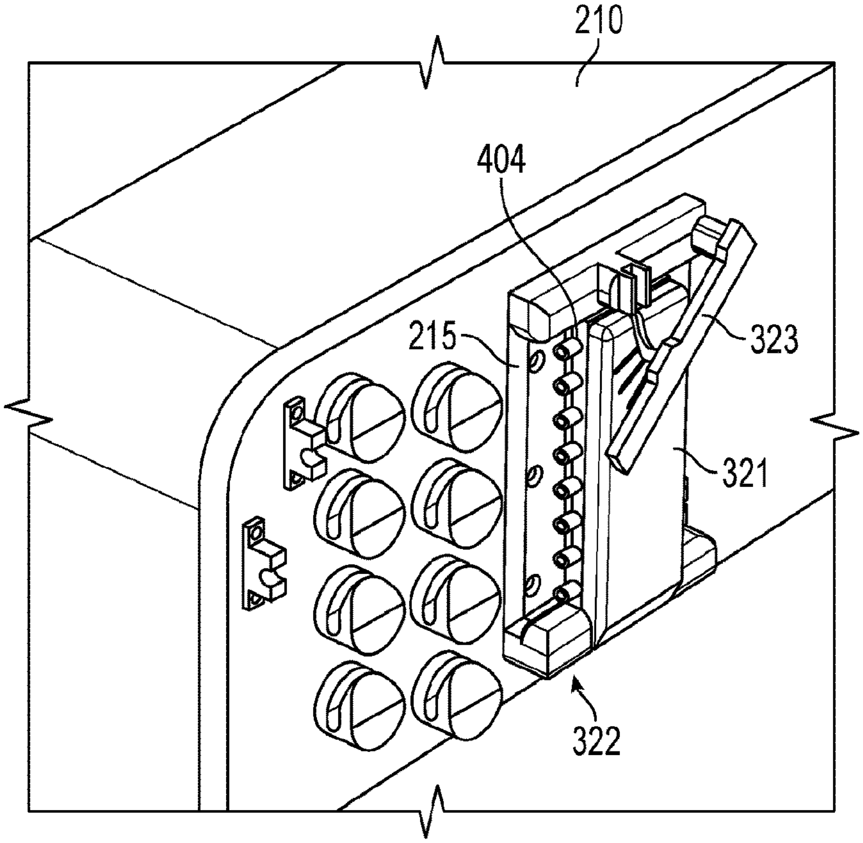

FIGS. 5A and 5B are partially schematic, perspective views of the cassette 404 of FIGS. 4A and 4B being installed within the mount 215 of FIGS. 3A-3C in accordance with various embodiments of the present technology. As shown in FIG. 5A, the alignment features 425 of the cassette 404 can be aligned with the alignment features 325 of the mount 215. The cassette 404 can then be advanced toward the mount 215 such that the alignment features 325 of the mount 215 engage with (e.g., are inserted into) the alignment features 425 of the cassette 404. As the alignment features 325 of the mount 215 engage with the alignment features 425 of the cassette 404, the cassette 404 can be positioned and/or laterally retained such that the device ID 455 (FIG. 4A) or the device ID 458 of the cassette 404 is aligned with, positioned proximate to, and/or brought with a field of view of the ID sensor 211 of the mount 215. As shown in FIG. 5B, the arm 321 of the mount 215 can then be swung or otherwise transitioned to a closed position, and the locking mechanism 323 of the mount 215 can be rotated over the arm 321 to releasably retain (a) the arm 321 in the closed position and (b) the cassette 404 within the mount 215. In turn, the ID sensor 211 of the mount 215 can read the device ID 455 or the device ID 458. As described in greater detail below with respect to FIG. 9, a reading of the device ID 455 or the device ID 458 produced by the ID sensor 211 can be used to determine whether the cassette is a counterfeit, has previously been used, and/or has expired.

In some embodiments, the cassette 404 can further include a membrane or diaphragm adhered or otherwise affixed to the cassette 404. For example, FIG. 5A illustrates a membrane 560 positioned between a body portion of the cassette 404 and the mount 215. The membrane 560 can include alignment features 525 (e.g., recesses) that (a) align with the alignment features 425 of the body portion of the cassette 404 and (b) engage or interface with the alignment features 325 of the mount 215. As discussed in greater detail below with respect to FIGS. 6A-6C, the membrane 560 can be used to hermetically seal the cavity 457 (FIG. 4A) and/or other fluid paths in the cassette 404. As such, should the membrane 560 be punctured or otherwise damaged to break the hermetic seal, the cassette 404 can be rendered inoperable for its intended purpose to control fluid flow through a disposable set (e.g., the disposable set 107 of FIG. 1A) during an exchange treatment of an APD system.

Referring again to FIGS. 3B and 3C, for example, the mount 215 can include (a) a plunger mechanism 330 that includes a point or puncture feature 335. The plunger mechanism 330 can (a) be positioned within an aperture 324 (e.g., a hole) or recess in the mount 215 and (b) be mechanically actuated (e.g., using circuits of the APD machine 210 of FIG. 2) to translate the plunger mechanism 330 between (i) a retracted position (as shown in FIG. 3C) at which the puncture feature 335 is positioned beneath a lip of the aperture 324 and (ii) an extended position (e.g., as shown in FIG. 6B) at which the puncture feature 335 is positioned above the lip of the aperture 324 (e.g., to puncture or otherwise damage a membrane 560 of a cassette 404 positioned within the mount 215).

Referring to FIG. 3C, the mount 215 in some embodiments can further include an installation sensor 340 having a protrusion or nub 341 and a spring 342 or other elastic member. In the absence of force, the spring 342 can be positioned in an expanded configuration such that the nub 341 juts out or is exposed above a contacting surface of the mount 215. In the presence of an applied force (e.g., from a cassette 404 or another component installed within the mount 215), the nub 341 can be pushed or translated downward to transition the spring 342 to a compressed configuration. In turn, sensing electronics (not shown) of the installation sensor 340 can detect compression of the spring 342 and thereby determine that a cassette 404 or another component is currently installed in the mount 215. In some embodiments, to ensure proper operation of the APD system during an exchange treatment, the APD machine 210 (FIG. 2) can be configured to execute the exchange treatment only when the installation sensor 340 determines a cassette 404 or another component is properly installed within the mount 215. In these and other embodiments, when the installation sensor 340 determines that a cassette 404 or another component is currently installed in the mount 215 and/or the locking mechanism 323 is rotated over the arm 321 of the mount 215 to retain the arm 321 in the closed position, the mount 215 can prevent (a) the arm 321 from opening or (b) the cassette 404 or the other component from being removed from the mount 215 before and/or until the plunger mechanism 330 is actuated (e.g., to puncture or otherwise damage the cassette 404 or other component). As described in greater detail below, this can ensure that the cassette 404 or the other component is rendered inoperable before it is released from the mount 215 such that the cassette 404 or other component cannot be reused in an APD system to execute future exchange treatments.

Figure 6A:
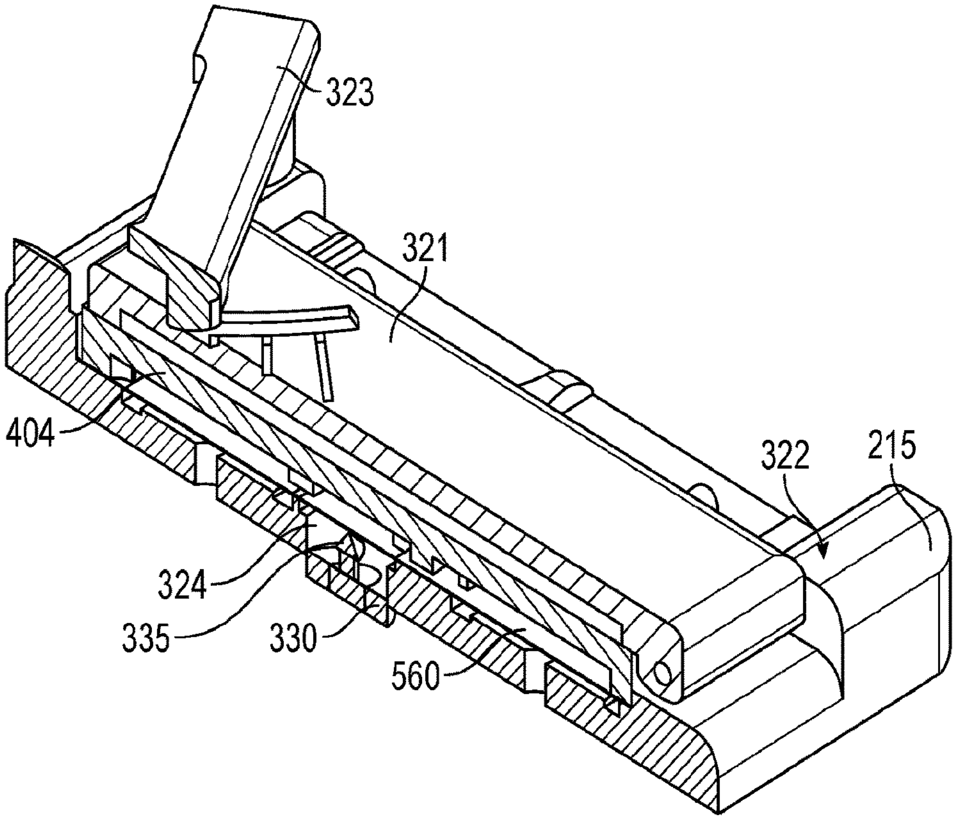
FIGS. 6A-6C are partially schematic, cross-sectional views of the cassette of FIGS. 4A and 4B installed within the mount of FIGS. 3A-3C in accordance with various embodiments of the present technology.
Figure 6B:
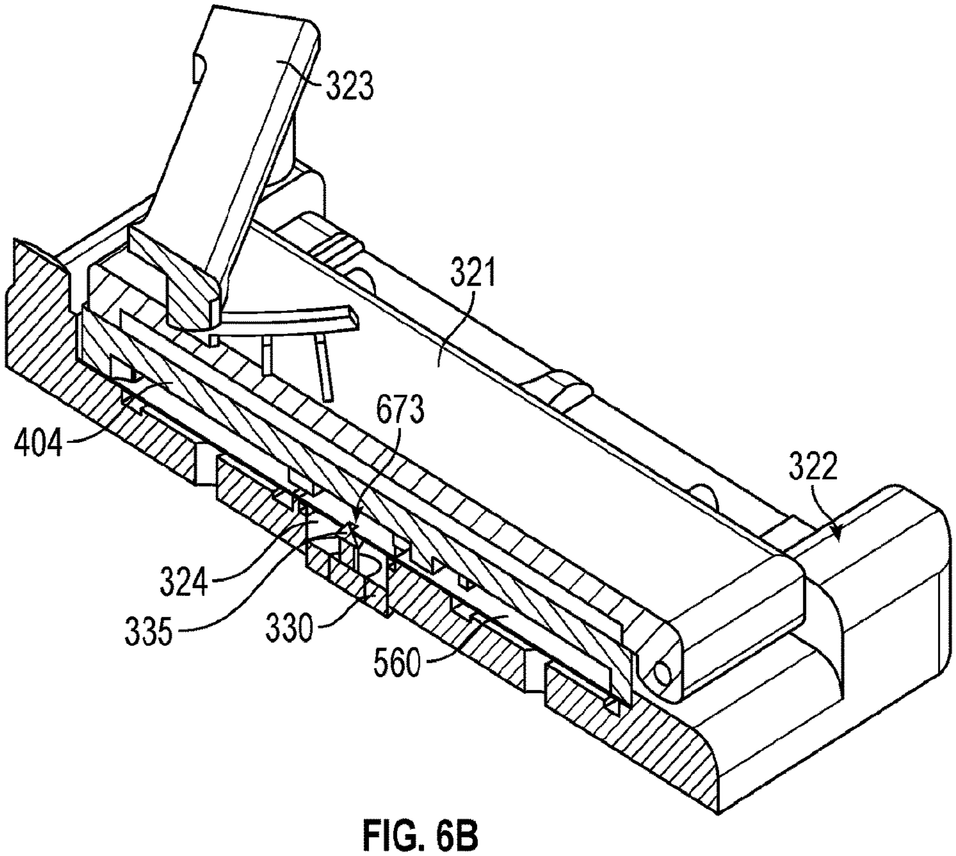
Figure 6C:
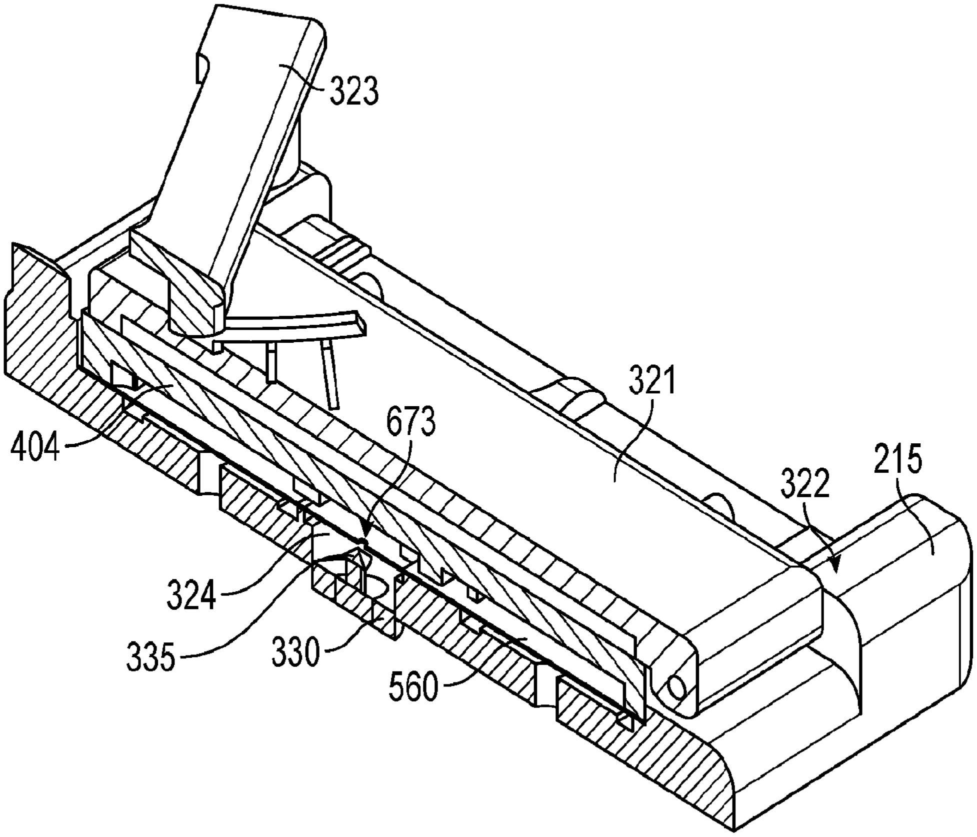

FIGS. 6A-6C are partially schematic, cross-sectional views of the cassette 404 of FIGS. 4A and 4B installed within the cassette mount 215 of FIGS. 3A-3C in accordance with various embodiments of the present technology. More specifically, FIGS. 6A-6C illustrate various states of the plunger mechanism 330 of the mount 215 as it is used to puncture the membrane 560 of the cassette 404. Referring to FIG. 6A, the cassette 404 is shown installed within the mount 215. The arm 321 of the mount 215 is in the closed position, and the locking mechanism 323 is rotated over the arm 321. In addition, the plunger mechanism 330 is shown in the retracted position such that the puncture feature 335 of the plunger mechanism 330 is positioned beneath a lip of the aperture 324 and is out of contact with (or is only slightly in contact with) the membrane 560 of the cassette 404.

In FIG. 6B, the plunger mechanism 330 has been translated to the extended position such that the puncture feature 335 is brought into contact with and punctures the membrane 560. As the puncture feature 335 punctures the membrane 560, the puncture feature 335 damages the membrane 560 by creating a hole 673 in the membrane 560. In turn, the plunger mechanism 330 breaks a hermetic seal provided by the membrane 560 to fluid paths within the cassette 404. As a result, the cassette 404 can no longer be used to perform an exchange treatment without solution from the cassette 404 through the hole 673. Additionally, because bacteria is now permitted to enter an interior of the cassette 404 via the hole 673, the cassette 404 can no longer provide a sterile fluid path to perform an exchange treatment. Thus, the cassette 404 cannot be reused in future exchange treatments. After the plunger mechanism 330 is actuated to puncture or otherwise damage the membrane 560, the plunger mechanism 330 can be translated back to its retracted position (as shown in FIG. 6C). In turn, the locking mechanism 323 can be released or rotated such that it is no longer positioned above the arm 321, and the arm 321 can be transitioned to the open position such that the cassette 404 can be removed from the mount 215.

In some embodiments, the mount 215 can include both the plunger mechanism 330 and the ID sensor 211. In other embodiments, the mount 215 can include either the plunger mechanism 330 or the ID sensor 211. In these and still other embodiments, the mount 215 can include the installation sensor 340 (FIG. 3C) in (a) embodiments including the plunger mechanism 330, (b) embodiments including the ID sensor 211, and/or (c) embodiments lacking the plunger mechanism 330 and the ID sensor 211.

Figure 7:
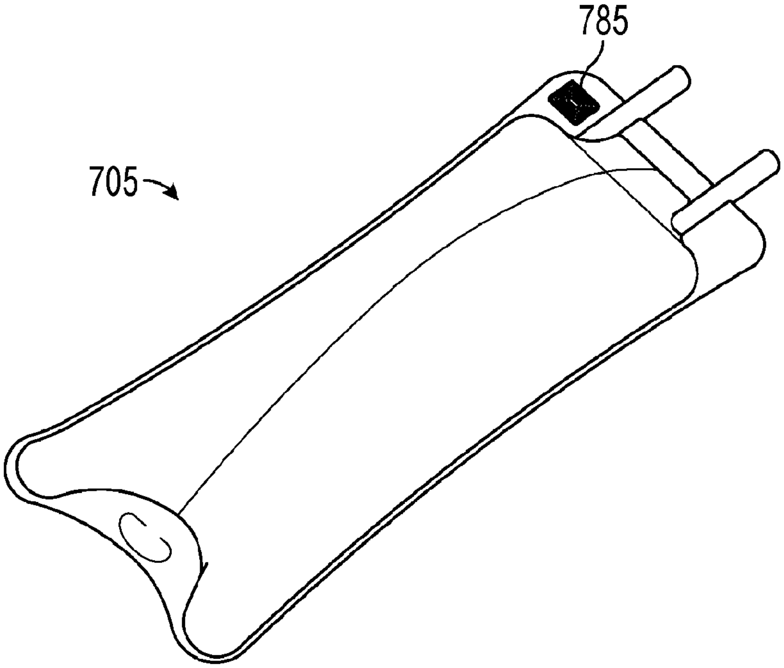
FIG. 7 is a partially schematic, perspective view of a source bag configured in accordance with various embodiments of the present technology.

Although the identification systems of the present technology are primarily discussed above in relation to cassettes, the identification systems of the present technology can be used in combination with other components (e.g., source bags, drain bags, damping devices, etc.) of an APD system. For example, FIG. 7 is a partially schematic, perspective view of a source bag 705 configured in accordance with various embodiments of the present technology. The source bag 705 can be the source bag 105 of FIG. 1A or another source bag of the present technology. The source bag 705 can be pre-filled with a solution (e.g., a dialysate) and sealed for use in an exchange treatment executed by an APD system. In some embodiments, the source bag 705 is manufactured from a medical-grade plastic compound and includes multiple ports for fluidly connecting the source bag 705 to other components of a disposable set (e.g., the disposable set 107 of FIG. 1A) via one or more fluid lines.

As shown, the source bag 705 includes a device identifier 785 ("the device ID 785") attached to, integrated into, and/or exposed through the source bag 705. Similar to the device IDs 455 and/or 458 of FIGS. 4A and 4B, respectively, the device ID 785 can be a small battery-operated identification device. Additionally, or alternatively, the device ID 785 can be an RFID device, a QR code, an NFC device, a digitally readable number, a marking, or another suitable identification device. The device ID 785 can be programmed or otherwise manufactured with an identifier unique to the source bag 705. For example, the device ID 785 can be assigned a unique identifier that is randomly generated and/or is based at least in part on (a) a date and/or time of day the source bag 705 was manufactured, marked, and/or filled with a solution; (b) a batch number corresponding to the source bag 705 and/or to the solution; (c) information (e.g., name, employee ID, etc.) related to a worker assigned to the batch, and/or (d) other information, such as a type of the solution and/or an expiration date of the solution. In some embodiments, the unique identifier can be encoded such that the device ID 785 can be read by only a manufacturer of the device ID 785, another authorized party (e.g., a licensee), and/or an ID sensor (e.g., the ID sensor 211 and/or 212 of FIG. 2) or identification system specifically configured to read the device ID 785.

Figure 8:
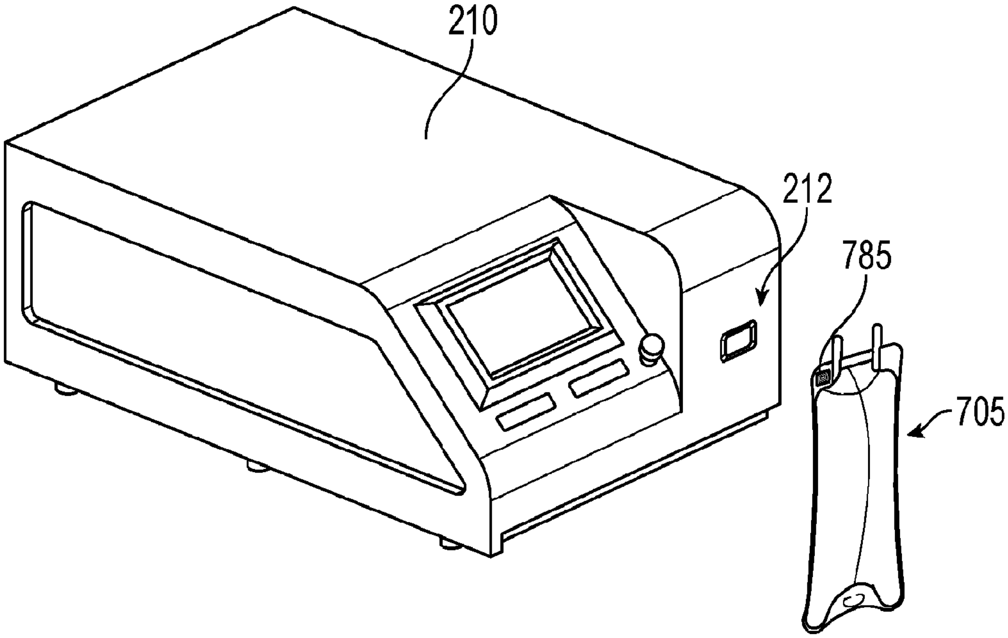
FIG. 8 is a partially schematic, perspective view of the APD machine of FIG. 2 and the source bag of FIG. 7.

FIG. 8 is a partially schematic, perspective view of the APD machine 210 of FIG. 2 and the source bag 705 of FIG. 7. As shown, the device ID 785 of the source bag 705 can be aligned with the ID sensor 212 (or the ID sensor 211 of FIG. 2) of the APD machine 210. In turn, the ID sensor 212 can read the device ID 785. As described in greater detail below with respect to FIG. 9, a reading of the device ID 785 produced by the ID sensor 212 can be used to determine whether the source bag 705 is a counterfeit, has previously been used, and/or has expired. Additionally, or alternatively, the device ID 785 can be used to determine whether the solution contained within the source bag 705 is a counterfeit, has previously been used, and/or has expired. If the APD system determines that the source bag 705 and/or the solution contained within the source bag 705 are counterfeits, have previously been used, and/or have expired, the APD system can prevent use of the source bag 705 and/or the solution in an exchange treatment executed by the APD system.

Figure 9:
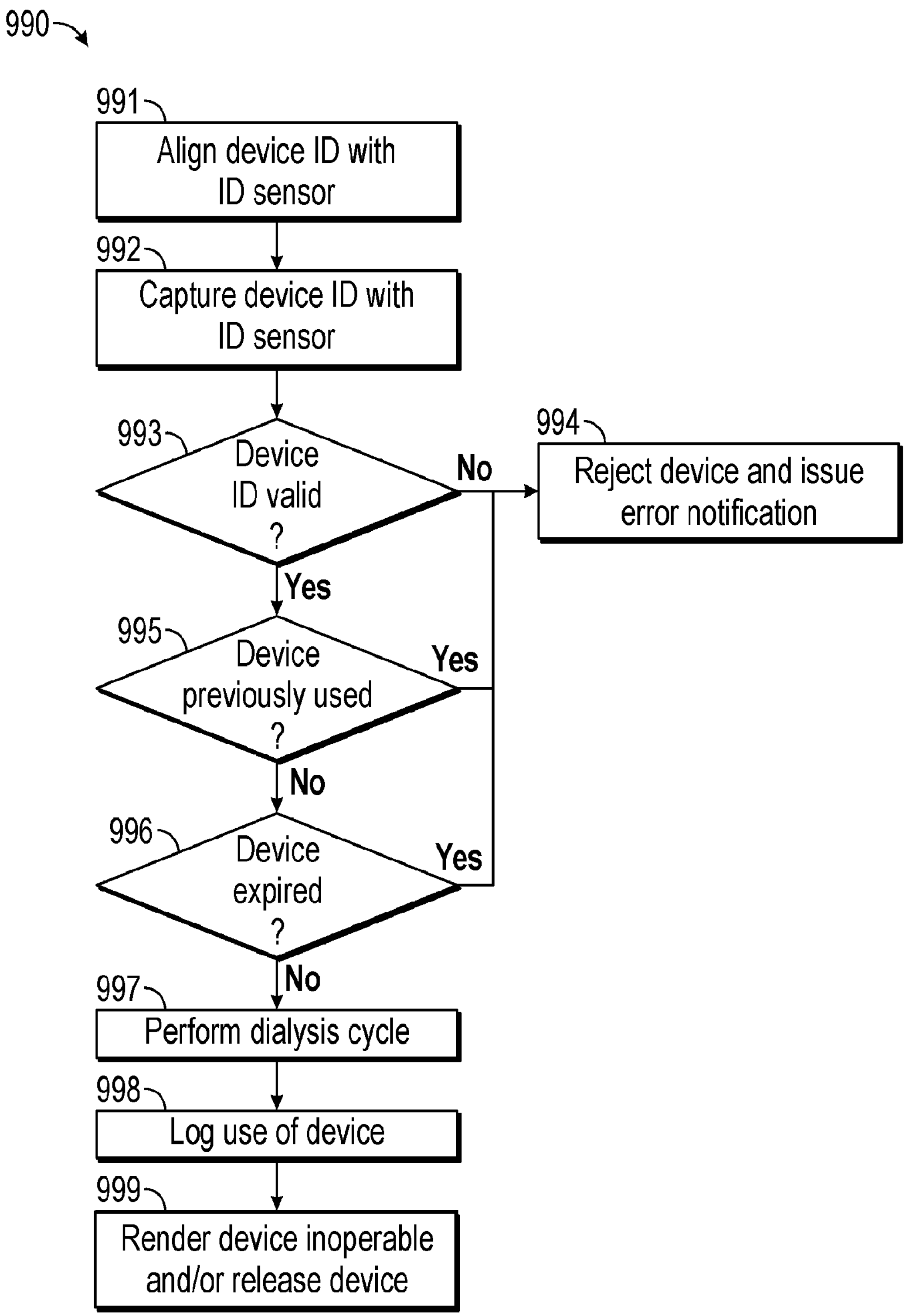
FIG. 9 is a flow diagram illustrating a method of operating an identification system in accordance with various embodiments of the present technology.

FIG. 9 is a flow diagram illustrating a method 990 of operating an identification system in accordance with various embodiments of the present technology. The method 990 is illustrated as a set of blocks, steps, operations, or processes 991-999. All or a subset of the blocks 991-999 can be executed at least in part by various components of a system, such as the APD system 100 of FIG. 1A. For example, all or a subset of the blocks 991-999 can be executed at least in part by an APD machine, a pump, an ID sensor, a mount, a plunger mechanism, an installation sensor, a device ID, a cassette, a source bag, a drain bag, a damping device, and/or other portions of a disposable set. Additionally, or alternatively, all or a subset of the blocks 991-999 can be executed at least in part by an operator (e.g., a user, a patient, a caregiver, a family member, a physician, etc.) of the system, one or more remote servers/databases (e.g., the one or more remote servers/databases 152 of FIG. 1B), and/or one or more computing devices (e.g., the one or more computing devices 151 of FIG. 1B). Furthermore, any one or more of the blocks 991-999 can be executed in accordance with the discussion above.

The method 990 begins at block 991 by aligning a device ID with an ID sensor. As discussed above, the device ID can be attached to, integrated with, exposed through, or otherwise associated with a cassette, a source bag, or another component of an APD system. In some embodiments, aligning a device ID with an ID sensor includes holding the device ID proximate and/or within a field of view of the ID sensor. In these and other embodiments, aligning a device ID within an ID sensor includes installing a cassette or another component of an APD system in a mount (e.g., of an APD machine). Installing the cassette or the other component of the APD system in the mount can include aligning alignment features of the cassette or other component with alignment features of the mount. Installing the cassette or the other component of the APD system in the mount can include (a) positioning the cassette or the other component of the APD system within the mount, (b) transitioning an arm of the mount into a closed position, and/or (c) engaging a locking mechanism of the mount. Installing the cassette or the other component of the APD system can include determining whether the cassette or the other component of the APD system is properly installed within the mount using an installation sensor of the mount.

At block 992, the method 990 continues by capturing or reading the device ID using the ID sensor. Capturing or reading the device ID can include capturing one or more images of the device ID. In these and other embodiments, capturing or reading the device ID can include receiving and/or processing a signal emitted or transmitted by the device ID. In these and still other embodiments, capturing or reading the device ID can include decoding information encoded within the device ID.

At block 993, the method 990 continues by determining whether the device ID captured or read at block 992 is valid. In some embodiments, determining whether the device ID is valid includes transmitting or sending the device ID to a remote server or processor using, for example, WiFi, ethernet, radio, and/or cellular networks. In these and other embodiments, determining whether the device ID is valid includes attempting to retrieve or match the device ID from/to a list of valid IDs stored in a database. For example, the device ID captured or read at block 992 can be cross-referenced against a whitelist of valid device IDs stored in a remote database and/or locally (e.g., on an APD machine of the system). Continuing with this example, the device ID captured or read at block 992 can be cross-referenced against the whitelist stored in the remote database, for example, when the APD system has internet access and can communicate with the corresponding remote servers/databases. Additionally, or alternatively, the device ID captured or read at block 992 can be cross-referenced against a whitelist stored locally at the APD system, for example, when the APD system lacks internet connectivity and/or is unable to communicate with the corresponding remote servers/databases. The whitelist stored locally at the APD system can be updated periodically (e.g., once a day, once a week, once a month, etc.) and/or whenever the APD system is able to communicate with the corresponding remote servers/databases. Additionally, or alternatively, the whitelist stored locally at the APD system can be periodically synced with the whitelist stored in the remote servers/databases (e.g., such that the whitelists are updated to reflect use or expiration of any cassettes, source bags, or other components of the APD system logged in either whitelist). The whitelists can be managed by a manufacturer or distributor of various components of the APD system.

In the event that the device ID captured and/or read at block 992 does not match a valid device ID stored in the whitelist(s), the method 990 can proceed to block 994. At block 994, the method 990 continues by rejecting use of the cassette, the source bag, or the other component corresponding to the device ID. Rejecting use of the cassette, the source bag, or the other component can include preventing the APD system from executing an exchange treatment using the cassette, the source bag, or the other component (e.g., until the cassette, the source bag, or the other components is replaced with a valid component of the APD system). In these and other embodiments, rejecting use of the cassette, the source bag, or the other component can include puncturing or otherwise damaging the cassette, the source bag, or the other component (e.g., consistent with the discussion of block 999 below) such that it cannot be used in an APD system. In these and still other embodiments, rejecting use of the cassette, the source bag, or the other component can include issuing an alert, alarm, or error notification to an operator of the APD system (e.g., via the APD machine, a user's computing device, etc.). In this manner, the method 990 can prevent use of counterfeit cassettes, source bags, or other components of the APD system.

Referring again to block 993, in the event that the device ID captured and/or read at block 992 matches a valid device ID stored in the whitelist(s), the method 990 can proceed to block 995. At block 995, the method 990 can continue by determining whether the cassette, the source bag, or the other component of the APD system corresponding to the device ID has been previously used. For example, the method 990 can store an indicator (e.g., in the whitelist(s)) indicating whether the cassette, the source bag, or the other component of the APD system has been previously used. If the method 990 determines that the cassette, the source bag, or the other component of the APD system has previously been used, the method 990 can proceed to block 994 to reject use of the cassette, the source bag, or the other component of the APD system. In this manner, the method 990 can prevent multiple uses of otherwise valid (e.g., non-counterfeit) cassettes, source bags, or other components of the APD system. On the other hand, if the method 990 determines that the cassette, the source bag, or the other components of the APD system has not previously been used, the method 990 can proceed to block 996.

At block 996, the method 990 continues by determining whether the cassette, the source bag, a solution included in the source bag, or the other component of the APD system has expired. For example, the method 990 can store (e.g., in the whitelist(s)) an expiration date associated with the cassette, the source bag, the solution included in the source bag, or the other component of the APD system. If the method determines that the cassette, the source bag, the solution contained in the source bag, or the other component of the APD system has expired, the method 990 can proceed to block 994 to reject use of the cassette, the source bag, the solution contained within the source bag, or the other component of the APD system. In this manner, the method 990 can prevent use of expired solution and/or components of the APD system in an exchange treatment executed by the APD system. On the other hand, if the method 990 determines that the cassette, the source bag, the solution contained within the source bag, or the other component of the APD system has not expired, the method 990 can proceed to block 997.

At block 997, the method 990 continues by executing an exchange treatment using the cassette, the source bag, the solution contained within the source bag, or the other component of the APD system. In some embodiments, executing the exchange treatment can include issuing an alert, alarm, or notification that the cassette, the source bag, the solution contained within the source bag, or the other component of the APD system is valid, new, and/or not expired.

At block 998, the method 990 continues by logging use of the cassette, the source bag, the solution contained within the source bag, or the other component of the APD system. In some embodiments, logging use of the cassette, the source bag, the solution contained within the source bag, or the other component of the APD system can include updating an indicator (e.g., stored in the whitelist(s)) associated with the device ID of the cassette, the source bag, the solution contained within the source bag, or the other component of the APD system to reflect that the cassette, the source bag, the solution contained within the source bag, or the other component of the APD system has been used in an exchange treatment. Thus, should an operator attempt to reuse the cassette, the source bag, the solution contained within the source bag, or the other component of the APD system in a future exchange treatment, the method 990 will be able to determine at block 995 and based at least in part on the updated indicator, that the cassette, the source bag, the solution contained within the source bag, or the other component of the APD system has previously been used. In turn, the method 990 will be able to reject at block 994 reuse of the cassette, the source bag, the solution contained within the source bag, or the other component of the APD system. This is expected to reduce, minimize, and/or eliminate unauthorized sale or resale of components of the APD system.

At block 999, the method 990 continues by rendering the cassette, the source bag, and/or the other component of the APD system corresponding to the device captured at block 992 inoperable for future use. For example, after an exchange treatment is complete, the method 990 can actuate a plunger mechanism to puncture or otherwise damage a membrane of a cassette positioned within a mount of the APD machine. In some embodiments, the method 990 can retain the cassette within the mount until the plunger mechanism has been actuated to damage the membrane of the cassette. In this manner, the method 990 can physically render the cassette or another component of the APD system (e.g., installed within the mount) inoperable for reuse in future exchange treatments.

Although the steps of the method 990 are discussed and illustrated in a particular order, the method 990 illustrated in FIG. 9 is not so limited. In other embodiments, the method 990 can be performed in a different order. In these and other embodiments, any of the steps of the method 990 can be performed before, during, and/or after any of the other steps of the method 990. For example, blocks 993-996 can be performed in any order. Additionally, or alternatively, block 998 can be performed before or during block 997. Moreover, a person of ordinary skill in the relevant art will recognize that the illustrated method 990 can be altered and still remain within these and other embodiments of the present technology. For example, one or more steps (e.g., blocks 996 and/or 999) of the method 990 illustrated in FIG. 9 can be omitted and/or repeated in some embodiments.

Although not shown so as to avoid unnecessarily obscuring the description of the embodiments of the technology, any of the devices, systems, and methods described above can include and/or be performed by a computing device configured to direct and/or arrange components of the systems and/or to receive, arrange, store, analyze, and/or otherwise process data received, for example, from the APD system and/or other components of the APD system (e.g., remote servers, remote databases, ID sensors, device IDs, user computing devices, installation sensors, etc.). As such, such a computing device includes the necessary hardware and corresponding computer-executable instructions to perform these tasks. More specifically, a computing device configured in accordance with an embodiment of the present technology can include a processor, a storage device, input/output device, one or more sensors, and/or any other suitable subsystems and/or components (e.g., displays, speakers, communication modules, etc.). The storage device can include a set of circuits or a network of storage components configured to retain information and provide access to the retained information. For example, the storage device can include volatile and/or non-volatile memory. As a more specific example, the storage device can include random access memory (RAM), magnetic disks or tapes, and/or flash memory.

The computing device can also include (e.g., non-transitory) computer readable media (e.g., the storage device, disk drives, and/or other storage media) including computer-executable instructions stored thereon that, when executed by the processor and/or computing device, cause the systems to perform one or more of the methods described herein. Moreover, the processor can be configured for performing or otherwise controlling steps, calculations, analysis, and any other functions associated with the methods described herein.

In some embodiments, the storage device can store one or more databases used to store data collected by the systems as well as data used to direct and/or adjust components of the systems. In one embodiment, for example, a database is an HTML file designed by the assignee of the present disclosure. In other embodiments, however, data is stored in other types of databases or data files.

One of ordinary skill in the art will understand that various components of the systems (e.g., the computing device) can be further divided into subcomponents, or that various components and functions of the systems may be combined and integrated. In addition, these components can communicate via wired and/or wireless communication, as well as by information contained in the storage media.

C. Examples

Several aspects of the present technology are set forth in the following examples. Although several aspects of the present technology are set forth in examples specifically directed to methods, systems, and computer-readable mediums; any of these aspects of the present technology can similarly be set forth in examples directed to any of systems, devices, methods, and computer-readable mediums in other embodiments.

1. A method of operating an automated peritoneal dialysis (APD) system, the method comprising:
   capturing a device identifier of a disposable component of the APD system;
   cross-referencing the device identifier with a whitelist of valid device identifiers; and
   based at least in part on the cross-referencing of the device identifier with the whitelist, determining whether to execute an exchange treatment using the disposable component.
2. The method of example 1 wherein capturing the device identifier includes scanning or reading the device identifier of the disposable component with an identification sensor of the APD system.
3. The method of example 1 or example 2 wherein cross-referencing the device identifier with the whitelist includes determining whether the device identifier is included in the whitelist of valid device identifiers.
4. The method of any of examples 1-3 wherein cross-referencing the device identifier with the whitelist includes determining whether an indicator included in the whitelist and associated with the device identifier indicates that the disposable component has previously been used.
5. The method of any of examples 1-4 wherein cross-referencing the device identifier with the whitelist includes determining whether the disposable component or a solution contained within the disposable component has expired.
6. The method of any of examples 1-5 wherein cross-referencing the device identifier with the whitelist includes cross-referencing the device identifier with a first whitelist stored in a database or server remote from an APD machine of the APD system.
7. The method of any of examples 1-6 wherein cross-referencing the device identifier with the whitelist includes cross-referencing the device identifier with a first whitelist stored locally on an APD machine of the APD system.
8. The method of example 7, further comprising periodically syncing the first whitelist stored locally on the APD machine with a second whitelist stored in a database remote from the APD machine.
9. The method of any of examples 1-8, further comprising:
   executing the exchange treatment using the disposable component; and
   updating an indicator stored in the whitelist and associated with the device identifier to reflect that the disposable component has previously been used.

10. The method of any of examples 1-8, further comprising preventing execution of the exchange treatment using the disposable component.

11. The method of any of examples 1-10 wherein capturing the device identifier includes receiving the disposable component within a mount of the APD system.

12. The method of example 11, further comprising physically damaging the disposable component such that the disposable component cannot be used in future exchange treatments.

13. The method of example 11 or example 12 wherein receiving the disposable component within the mount includes receiving the disposable component within the mount such that the disposable component cannot be readily removed from the mount until after the disposable component is physically damaged and rendered inoperable for use in future exchange treatments.

14. An automated peritoneal dialysis (APD) system, comprising:

an identification system including an identification sensor configured to read a device identifier included on a disposable component, wherein the disposable component is configured to introduce or remove solution from a patient during an exchange treatment of the APD system, wherein the identification system is configured to determine whether to execute the exchange treatment using the disposable component based, at least in part, on the device identifier.

15. The APD system of example 14, further comprising a mount configured to receive the disposable component.

16. The APD system of example 15 wherein the identification sensor is disposed on, integrated with, or exposed through the mount.

17. The APD system of example 15 or example 16 wherein:

the disposable component includes a membrane;

the mount includes a plunger mechanism having a puncture feature; and the plunger mechanism is mechanically actuatable to puncture the membrane of the disposable component at least when the disposable component is installed in the mount.

18. The APD system of example 17 wherein:

the mount further includes an installation sensor configured to determine when the disposable component is installed in the mount; and when the installation sensor determines that the disposable component is installed in the mount, the mount is configured to lock such that the disposable component is retained within the mount at least until the plunger mechanism is mechanically actuated to puncture the membrane.

19. The APD system of any of examples 14-18 wherein the disposable component includes a cassette.

20. The APD system of example 19 wherein the device identifier is a radiofrequency identification (RFID) device, a quick response (QR) code, a near-field communication (NFC) device, or a digitally readable number.

21. The APD system of example 19 wherein the device identifier is a marking of text on a surface of the cassette.

22. The APD system of example 14 wherein:

the disposable component is a source bag containing the solution; and the device identifier indicates an expiration date of the solution.

23. The APD system of any of examples 14-22 wherein the identification sensor is an image sensor, a camera, a scanner, a radiofrequency (RF) receiver, or a near-field communication (NFC) reader.

24. The APD system of any of examples 14-23, further comprising one or more remote servers or databases storing a whitelist of valid device identifiers.

25. The APD system of any of examples 14-24, further comprising an APD machine configured to (a) store a local copy of a whitelist of valid device identifiers stored on one or more remote servers or databases and (b) periodically sync the local copy with the whitelist of valid device identifiers stored on one or more servers or databases remote from the APD machine.

26. A non-transitory, computer-readable medium having instructions stored thereon that, when executed by one or more processors of an automated peritoneal dialysis (APD) system, cause the APD system to perform a method comprising:

capturing a device identifier of a disposable component of the APD system;

cross-referencing the device identifier with a whitelist of valid device identifiers; and based at least in part on the cross-referencing of the device identifier with the whitelist, determining whether to execute an exchange treatment using the disposable component.

C. Conclusion

From the foregoing, it will be appreciated that specific embodiments of the technology have been described herein for purposes of illustration, but well-known structures and functions have not been shown or described in detail to avoid unnecessarily obscuring the description of the embodiments of the technology. To the extent any materials incorporated herein by reference conflict with the present disclosure, the present disclosure controls. Where the context permits, singular or plural terms can also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. As used herein, the phrase "and/or" as in "A and/or B" refers to A alone, B alone, and both A and B. Where the context permits, singular or plural terms can also include the plural or singular term, respectively. Additionally, the terms "comprising," "including," "having" and "with" are used throughout to mean including at least the recited feature(s) such that any greater number of the same feature and/or additional types of other features are not precluded.

Furthermore, as used herein, the team "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. Moreover, the terms "connect" and "couple" are used interchangeably herein and refer to both direct and indirect connections or couplings. For example, where the context permits, element A "connected" or "coupled" to element B can refer (i) to A directly "connected" or directly "coupled" to B and/or (ii) to A indirectly "connected" or indirectly "coupled" to B.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments can perform steps in a different order. As another example, various components of the technology can be further divided into subcomponents, and/or various components and/or functions of the technology can be combined and/or integrated. Furthermore, although advantages associated with certain embodiments of the technology have been described in the context of those embodiments, other embodiments can also exhibit such advantages, and not all embodiments need necessarily exhibit such advantages to fall within the scope of the technology.

It should also be noted that other embodiments in addition to those disclosed herein are within the scope of the present technology. For example, embodiments of the present technology can have different configurations, components, and/or procedures in addition to those shown or described herein. Moreover, a person of ordinary skill in the art will understand that these and other embodiments can be without several of the configurations, components, and/or procedures shown or described herein without deviating from the present technology. Accordingly, the disclosure and associated technology can encompass other embodiments not expressly shown or described herein.

What is claimed is:

1. An automated peritoneal dialysis (APD) system, comprising:

a transfer set comprising disposable components configured to introduce or remove solution from a patient during an exchange treatment of the APD system, the disposable components comprising a cassette and a source bag containing the solution; and an identification system comprising one or more identification sensors, the one or more identification sensors configured to read a device identifier included on at least one of the disposable components, wherein the identification system is configured to determine whether to execute the exchange treatment using the cassette based, at least in part, on the device identifier of the cassette.

2. The APD system of claim 1, further comprising a mount configured to receive the cassette.

3. The APD system of claim 2, wherein the one or more identification sensors are is disposed on, integrated with, or exposed through the mount.

4. The APD system of claim 2, wherein:

the cassette includes a membrane;

the mount includes a plunger mechanism having a puncture feature; and the plunger mechanism is mechanically actuatable to puncture the membrane of the cassette at least when the cassette is installed in the mount.

5. The APD system of claim 4, wherein:

the mount further includes an installation sensor configured to determine when the cassette is installed in the mount; and when the installation sensor determines that the cassette is installed in the mount, the mount is configured to lock such that the cassette is retained within the mount at least until the plunger mechanism is mechanically actuated to puncture the membrane.

6. The APD system of claim 1, wherein the one or more identification sensors are configured to read the device identifiers of the cassette and the source bag.

7. The APD system of claim 1, wherein the device identifier is a radiofrequency identification (RFID) device, a quick response (QR) code, a near-field communication (NFC) device, or a digitally readable number.

8. The APD system of claim 1, wherein the device identifier is a marking of text on a surface of the cassette.

9. The APD system of claim 6, wherein the device identifier indicates an expiration date of the solution.

10. The APD system of claim 1, wherein the one or more identification sensors are an image sensor, a camera, a scanner, a radiofrequency (RF) receiver, or a near-field communication (NFC) reader.

11. The APD system of claim 1, further comprising one or more remote servers or databases storing a whitelist of valid device identifiers.

12. The APD system of claim 1, further comprising an APD machine configured to (a) store a local copy of a whitelist of valid device identifiers stored on one or more remote servers or databases and (b) periodically sync the local copy with a whitelist of valid device identifiers stored on one or more servers or databases remote from the APD machine.

13. A method of operating the APD system of claim 1, the method comprising:

validating the device identifier included on the cassette; and executing the exchange treatment using the cassette in response to validating the device identifier.

14. The method of claim 13, wherein validating the device identifier comprises validating the device identifier with the identification system.

15. The method of claim 13, wherein validating the device identifier comprises validating the device identifier with the one or more identification sensors that are disposed on, integrated with, or exposed through a mount of the APD system.

16. The method of claim 13, further comprising placing the cassette on a mount of the APD system prior to validating the device identifier.

17. The method of claim 13, further comprising:

storing a local copy of a whitelist of valid device identifiers stored on one or more remote servers or databases and syncing the local copy with a whitelist of valid device identifiers stored on one or more servers or databases remote from the APD system.

18. The method of claim 13, further comprising:

making a determination that the cassette is installed in a mount of the APD system; and locking the cassette within the mount in response to making the determination.

19. The method of claim 13, wherein validating the device identifier comprises validating the device identifier in a form of a radiofrequency identification (RFID) device, a quick response (QR) code, a near-field communication (NFC) device, or a digitally readable number.

20. A non-transitory computer readable medium storing instructions that, when executed by the APD system of claim 1, cause the APD system to perform functions comprising:

validating the device identifier included on the cassette; and executing the exchange treatment using the cassette in response to validating the device identifier.

21. The APD system of claim 1, wherein the identification system comprises a first identification sensor for reading the device identifier of the cassette and a second identification sensor for reading the device identifier of the source bag, wherein the identification system is further configured to determine whether to execute the exchange treatment using the source bag based, at least in part, on the device identifier of the source bag.

* * * * *